United States Patent [19]
Bocek et al.

[11] Patent Number: 5,251,624
[45] Date of Patent: Oct. 12, 1993

[54] PULSE GENERATOR FOR USE IN AN IMPLANTABLE ATRIAL DEFIBRILLATOR

[75] Inventors: Joseph M. Bocek, Seattle; Kenneth R. Infinger, Redmond; Darrell O. Wagner, Monroe, all of Wash.

[73] Assignee: InControl, Inc., Redmond, Wash.

[21] Appl. No.: 902,998

[22] Filed: Jun. 22, 1992

[51] Int. Cl.$^5$ .............................................. A61N 1/36
[52] U.S. Cl. ...................................................... 607/6
[58] Field of Search ........ 128/419 D, 419 PG, 419 P, 128/908

[56] References Cited

U.S. PATENT DOCUMENTS 5,048,521  9/1991  Pless et al. ................. 128/419 PG
5,111,816  5/1992  Pless et al. ................. 128/419 PG Primary Examiner—William E. Kamm
Assistant Examiner—George Manuel
Attorney, Agent, or Firm—Foley & Lardner

[57] ABSTRACT

A pulse generator for use in implantable atrial defibrillator provides cardioverting electrical energy to the atria of a heart through at least one lead having a pair of electrodes associated with the atria of the heart. The pulse generator includes a depletable, low voltage, power source such as a battery. A charging circuit coupled to the battery includes a flyback transformer for converting the battery voltage to low duty cycle pulsating high voltage electrical energy to store the high voltage electrical energy in a storage capacitor coupled to the charging circuit. A crosspoint switch selectively couples the storage capacitor to the electrodes for applying a portion of the stored electrical energy to the atria of the heart for cardioverting the atria of the heart.

66 Claims, 6 Drawing Sheets

PULSE GENERATOR FOR USE IN AN IMPLANTABLE ATRIAL DEFIBRILLATOR

BACKGROUND OF THE INVENTION

The present invention generally relates to an automatic implantable atrial defibrillator for delivering cardioverting or defibrillating electrical energy to the atria of a human heart. The present invention is more particularly directed to a pulse generator for use in an automatic implantable atrial defibrillator which provides the cardioverting or defibrillating electrical energy while exhibiting reduced power consumption of a depletable power source, such as a battery, within the atrial defibrillator.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistent to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

An implantable defibrillator must be powered by a portable, depletable power source, such as a battery. It has been long believed that as much electrical energy is required to cardiovert or defibrillate the atria of the heart as is required to cardiovert or defibrillate the ventricles of the heart, on the order of ten joules or more. In addition, episodes of atrial fibrillation occur much more frequently than do episodes of ventricular fibrillation. As a result, due to the contemplated required cardioverting or defibrillating energy levels for cardioverting or defibrillating the atria of the heart and the predicted required frequency of delivering such energies, it has long been believed that an implantable atrial defibrillator would deplete its power source so rapidly that frequent battery replacement would be required. Since battery replacement would require the surgical explanting of the defibrillator, it has long been believed that an implantable atrial defibrillator could not be a commercial reality. To this day, a commercially implantable atrial defibrillator remains unavailable.

Defibrillators generally include a means, such as a storage capacitor, for storing the electrical energy required to cardiovert or defibrillate the heart. Since ventricular fibrillation is life threatening, a ventricular defibrillator must charge its storage capacity quickly to permit essentially immediate cardioversion. Such quick storage capacitor charging places an extreme drain on a defibrillator battery thereby limiting the number of times that an implantable ventricular defibrillator can deliver cardioverting or defibrillating energy. This however does not impact upon the commercial nature of such defibrillators because ventricular fibrillation is life threatening and occurs rather infrequently. However, such charging methods believed necessary for an implantable atrial defibrillator has further added to the heretofore non-commercial nature of these devices.

In summary, the previously, believed requirements of quick storage capacitor charging, frequent storage capacitor charging, and high cardioverting defibrillating energy levels attributed to implantable atrial defibrillators has resulted in little or no development by others of a commercially feasible implantable atrial defibrillator. Hence, there remains a need in the art for a commercially viable atrial defibrillator.

The pulse generator of the present invention for use in an implantable atrial defibrillator represents a significant advancement towards a commercially viable implantable atrial defibrillator. The pulse generator of the present invention conserves battery power while still providing adequate electrical energy to cardiovert or defibrillate the atria of the heart to arrest atrial fibrillation. The pulse generator of the present invention achieves this end through the recognition that unlike ventricular fibrillation, atrial fibrillation is not life threatening. Hence, the pulse generator of the present invention charges its storage capacitor comparatively slowly to minimize drain on the defibrillator battery but in sufficient time to arrest the atria fibrillation. This is accomplished by converting the rather low voltage of about three volts provided by the battery to a low duty cycle pulsating high voltage of 300 to 400 volts, for example, for charging the storage capacitor. As disclosed herein in connection with the preferred embodiment, the pulsating high voltage is provided by a flyback transformer coupled to an oscillator which provides a high frequency, low duty cycle output. By virtue of this arrangement, sufficient electrical energy for cardioverting or defibrillating the heart is stored in the storage capacitor without imposing the high drain on the defibrillator battery previously caused by prior art quick charging methods. Even though a minute may be required to fully charge the storage capacity, this is sufficient time to arrest the atrial fibrillation and bring comfort to the patient. The end result is an implantable atrial defibrillator which is commercially viable since it is capable of providing a substantially increased number of cardioverting or defibrillating deliveries of electrical energy before replacement of the defibrillator battery is required.

In addition to the foregoing, the pulse generator of the present invention preferably includes a crosspoint switch for delivering the cardioverting or defibrillating electrical energy from the storage capacitor with a biphasic waveform. Such a biphasic waveform is believed to reduce energy requirements for cardioverting or defibrillating the atria of the heart to further reduce power consumption of the defibrillator battery. Other features and advantages of the present invention shall become apparent hereinafter.

SUMMARY OF THE INVENTION

The invention provides a pulse generator for use in an implantable atrial defibrillator for providing cardioverting electrical energy to the atria of a heart through lead means associated with the atria of the heart. The pulse generator includes a depletable, low-voltage, power source and charging means coupled to the power source. The charging means includes a charging circuit for converting the power source low voltage to low duty cycle pulsating high voltage electrical energy and storage capacitor means coupled to the charging circuit for storing the high voltage electrical energy. The pulse generator further includes switch means for selectivity coupling the storage capacitor means to the lead means for applying a portion of the stored electrical energy to the atria of the heart through the lead means for cardioverting the atria of the heart.

The present invention also provides an implantable atrial defibrillator for providing cardioverting electrical energy to the atria of a heart. The atrial defibrillator includes lead means associated with the atria of the heart and a battery for providing battery voltage. The atrial defibrillator further includes charging means coupled to the battery. The charging means includes storage capacitor means for storing electrical energy and a charging circuit for converting the battery voltage to low duty cycle pulsating high voltage electrical energy for slowly storing electrical energy in the storage capacitor means to a level for cardioverting the atria of the heart. The charging circuit stores the electrical energy in the storage capacitor means to the level in a time greater than about one minute. The atrial defibrillator further includes switch means for applying a portion of the stored electrical energy to the lead means for cardioverting the atria of the heart.

BRIEF DESCRIPTION OF THE PREFERRED EMBODIMENTS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
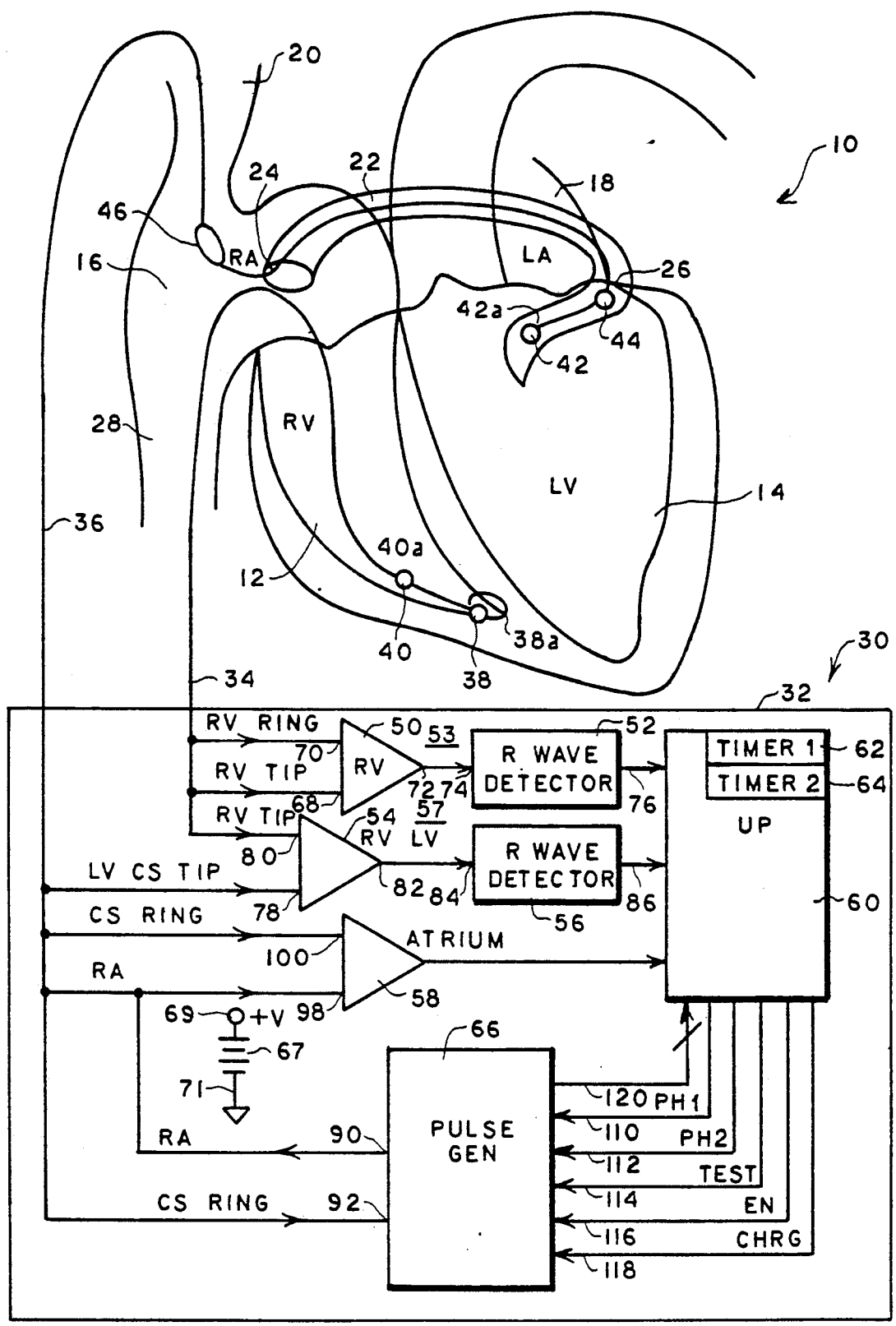
FIG. 1 is a schematic block diagram of a fully implantable atrial defibrillator embodying the present invention.

Referring now to FIG. 1 it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26, and the inferior vena cava 28. In addition, as used herein, the term "depolarization activation waves" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator, an endocardial first lead 34, and an intravascular second lead 36. The enclosure 32 and first and second leads 34 and 36 are arranged to be implanted beneath the skin of a patient so as to render the atrial defibrillator 30 fully implantable.

The endocardial first lead 34 preferably comprises an endocardial bi-polar lead having electrodes 38 and 40 arranged for establishing electrical contact with the right ventricle 12 of the heart 10. The electrodes 38 and 40 permit bi-polar sensing of depolarization activation waves in the right ventricle between a first pair of locations 38a and 40a within the right ventricle 12. As illustrated, the lead 34 is fed through the inferior vena cava 28, into the right atrium 16, and then into the right ventricle 12. As will be appreciated by those skilled in the art, a second path for lead 34 could alternatively be through the superior vena cava 20, into the right atrium 16, and then into the right ventricle 12.

The second lead 36 generally includes a first or distal electrode 42, a second or ring electrode 44, and a third electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or distal electrode 42 is within the coronary sinus or within a coronary vein, such as the great vein of the heart (not shown) adjacent the left ventricle 14. The electrodes 42, 44, and 46 are spaced apart such that when the first electrode 42 is within the coronary sinus 22 or a coronary vein adjacent the left ventricle 14, the second electrode 44 is beneath the left atrium 18 near the left ventricle 14 and the third electrode 46 is within the right atrium 16.

The first electrode 42 of the second lead 36 and the electrode 38 of the first lead 34 permit bi-polar sensing of depolarization activation waves between a second pair of locations 38a and 42a of the heart. Alternatively, the second pair of electrodes may include electrodes 42 and 40 and, as a result, the second pair of locations may be locations 42a and 40a. As will be noted in FIG. 1, the spacing between the second pair of locations 38a and 42a is greater than the spacing between the first pair of locations 38a and 40a. These relative spacings between the first and second pairs of locations between which depolarization activation waves are sensed enable reliable detection of depolarization activation waves.

The second electrode 44 together with the third electrode 46 of the second lead 36 provide for the delivery of defibrillating or cardioverting electrical energy to the atria. Because the second electrode 44 is located beneath the left atrium 18 near the left ventricle 14 and the third electrode 46 is within the right atrium 16, the electrical energy applied between these electrodes will be substantially confined to the atria 16 and 18 of the heart 10. Hence, the lead 36 forms a lead means associated with the atria 16 and 18 of the heart 10 for applying the defibrillating or cardioverting electrical energy to the heart.

Within the enclosure 32, the atrial defibrillator 30 includes a first sense amplifier 50, a first R wave detector 52, a second sense amplifier 54, a second R wave detector 56 and a third sense amplifier 58. Within the enclosure 32, the atrial defibrillator 30 also includes a microprocessor 60, a pulse generator 66, and a depletable, low voltage, power source or battery 67. The battery 67 includes a positive terminal 69 which may be coupled to the various internal components of the defibrillator 30 and a negative terminal 71 coupled to common potential. The battery 67 provides power to the various components at a low voltage of, for example, three volts.

The first sense amplifier 50 includes a first input 68 which is coupled to electrode 38 of the first lead 34 and a second input 70 which is coupled to electrode 40 of the first lead 34. The first sense amplifier 50 thus senses the electrical activity of the heart 10 between the first pair of locations of the heart 38a and 40a. It amplifies the sensed electrical activity of the heart and provides at an output 72 an amplified signal or first electrocardiogram representative of the electrical activity of the heart sensed by the bi-polar electrodes 38 and 40.

The first R wave detector 52 includes an input 74 which is coupled to the output 72 of the first amplifier 50. The R wave detector 52 includes a threshold detecting means or circuit which provides a substantially constant first electrical output having a duration substantially equal to the duration of the depolarization activation waves (R waves) sensed between electrodes 38 and 40. As a result, the electrodes 38 and 40 and the first sense amplifier 50 form a first sensing means 53 for sensing electrical activity of the heart including depolarization activation waves between the first pair of spaced apart locations of the heart 38a and 40a. The first R wave detector 52 forms a first output means for isolating the R wave feature of the first electrocardiogram and for producing a first electrical output, at output 76, having a first predetermined characteristic or duration corresponding and substantially equal to the duration of the depolarization activation waves (R waves) sensed between the first pair or locations of the heart 38a and 40a.

The second sense amplifier 54 includes a first input 78 which is coupled to the electrode 42 of the second lead 36 and a second input 80 which is coupled to electrode 38 of the first lead 34. As a result, the second sense amplifier 54 senses the electrical activity of the heart between the second pair of locations of the heart 38a and 42a. It provides at an output 82 an amplified signal or second electrocardiogram representative of the electrical activity of the heart sensed between the second pair of locations of the heart 38a and 42a.

The second R wave detector 56 includes an input 84 for receiving the amplified signal provided from the output 82 of the second sense amplifier 54. The second R wave detector 56 also includes a second threshold detecting means or circuit for providing a substantially constant second electrical output at output 86 having a duration substantially equal to the duration of the depolarization activation waves sensed by the second sense amplifier 54. As a result, electrode 42, electrode 38, and sense amplifier 54 form a second sensing means 57 for sensing electrical activity of the heart including depolarization activation waves between the second pair of locations of the heart 38a and 42a. The second R wave detector 56 forms a second output means for isolating the R wave feature of the second electrocardiogram for producing a second electrical output having a second predetermined characteristic or duration corresponding and substantially equal to the duration of the depolarization activation waves (R waves) sensed between the second pair of locations of the heart 38a and 42a.

A first timer 62 of microprocessor 60 times the duration of the first electrical output of the first electrical output provided by the first R wave detector 52 for timing the duration of a depolarization activation wave (R wave) sensed between the first pair of locations 38a and 40a. A second timer 64 of microprocessor 60 also times the duration of the second electrical output provided by the second R wave detector 56 for timing the duration of the same depolarization activation wave (R wave) sensed between the second pair of locations 42a and 38a. Since the spacing between the second pair of locations 42a and 38a is greater than the spacing between the first pair of locations 40a and 38a, if the electrical activity of the heart sensed by the first sensing means 53 and second sensing means 57 is a true depolarization activation wave (R wave), the duration of the second electrical output provided by R wave detector 56 will be longer than the duration of the first electrical output provided by the first R wave detector 52. Hence, the predetermined features (R waves) of the first and second electrocardiograms and more specifically, the first and second predetermined characteristics (durations) of those features will be different.

The microprocessor 60 reliably detects a depolarization activation wave when the second electrical output has a duration which is longer than the duration of the first electrical output. If the electrical activity of the heart sensed by the first and second sensing means 53 and 57 respectively is noise, the duration of the first and second electrical outputs will be substantially the same. Hence, in the foregoing manner the atrial defibrillator 30 reliably detects electrical activations (R waves) of the heart 10, even in an environment of electrical noise.

As described in copending U.S. application Ser. No. 07/685,130, filed Apr. 12, 1991, in the names of John M. Adams and Clifton A. Alferness and entitled ATRIAL DEFIBRILLATOR AND METHOD, which application is assigned to the assignee of the present invention and incorporated herein by reference, the microprocessor 60 utilizes the intervals between the detected R waves to determine if atrial fibrillation might be present. If such criteria are met, the microprocessor 60 activates the third sense amplifier 58 for sensing electrical activity in the atria 16 and 18 of the heart 10. To that end, the third sense amplifier 58 includes a first input 98 which is coupled to electrode 46 and a second input 100 which is coupled to electrode 44. The third sense amplifier 58 includes an output 102 which is coupled to the microprocessor 60 for providing the microprocessor 60 with an amplified signal representing the electrical activity of the atria 16 and 18 of the heart.

The microprocessor 60, as described in the aforementioned copending U.S. application Ser. No. 07/685,130, digitizes the amplified electrical signal provided by the third sense amplifier 58 and processes the digitized values of the atrial activity for detecting and confirming the presence of atrial fibrillation. Such atrial fibrillation detection may be implemented by the microprocessor 60 as described in the aforementioned copending application. Alternatively, the microprocessor 60 may be implemented in accordance with the atrial fibrillation detection algorithms disclosed in a paper: Janice Jenkins, Ki Hong Noh, Alain Guezennec, Thomas Bump, and Robert Arzbaecher, "Diagnosis of Atrial Fibrillation Using Electrograms from Chronic Leads: Evaluation of Computer Algorithms," PACE, Vol. 11, pp. 622-631, May 1988. Implementing such algorithms by a microprocessor such as microprocessor 60 is well within the purview of one skilled in the art.

The pulse generator 66 is coupled to the microprocessor 60 over a plurality of control lines 110, 112, 114, 116, and 118 and a multiple-bit bus 120. The pulse generator 66 includes a first output 90 which is coupled to electrode 46 of lead 36 and a second output 92 coupled to electrode 44 of lead 36. As will be seen hereinafter, the pulse generator 66 is responsive to control signals received over the control lines 110, 112, 114, 116, and 118 to store cardioverting or defibrillating electrical energy within a storage capacitor. Once the storage capacitor has been charged to a desired level, the pulse generator 66 responsive to control signals received over lines 116, 110, and 112, discharges the storage capacitor from outputs 90 and 92 to apply cardioverting or defibrillating electrical energy to the electrodes 46 and 44. As will be seen further hereinafter, the pulse generator 66 includes a crosspoint switch which is operable for applying the cardioverting or defibrillating electrical energy to electrodes 46 and 44 with a biphasic waveform having first and second phases. In the first phase, electrode 46 is made positive with respect to electrode 44 and in the second phase, electrode 44 is made positive with respect to electrode 46. In addition, the first and second phases of the biphasic waveform are preferably equal in duration of, for example, three milliseconds.

Control line 118 conducts a charge control signal to the pulse generator 66 to cause a charging circuit within pulse generator 66 to store the electrical energy within the storage capacitor. Control line 116 conducts an enable control signal to the pulse generator 66 to cause the pulse generator 66 to close an enable switch which couples the storage capacitor to the aforementioned crosspoint switch. Control lines 110 and 112 conduct control signals to the pulse generator 66 for controlling the delivery of the cardioverting or defibrillating electrical energy to outputs 90 and 92 in accordance with the aforementioned biphasic waveform. Lastly, control line 114 conducts a test control signal to the pulse generator 66 to cause the pulse generator 66 to discharge the storage capacitor internally within the pulse generator 66 for test purposes. Such testing may also be performed at periodic intervals for reforming the dielectric o the internal storage capacitor of the pulse generator 66.

Figure 2:
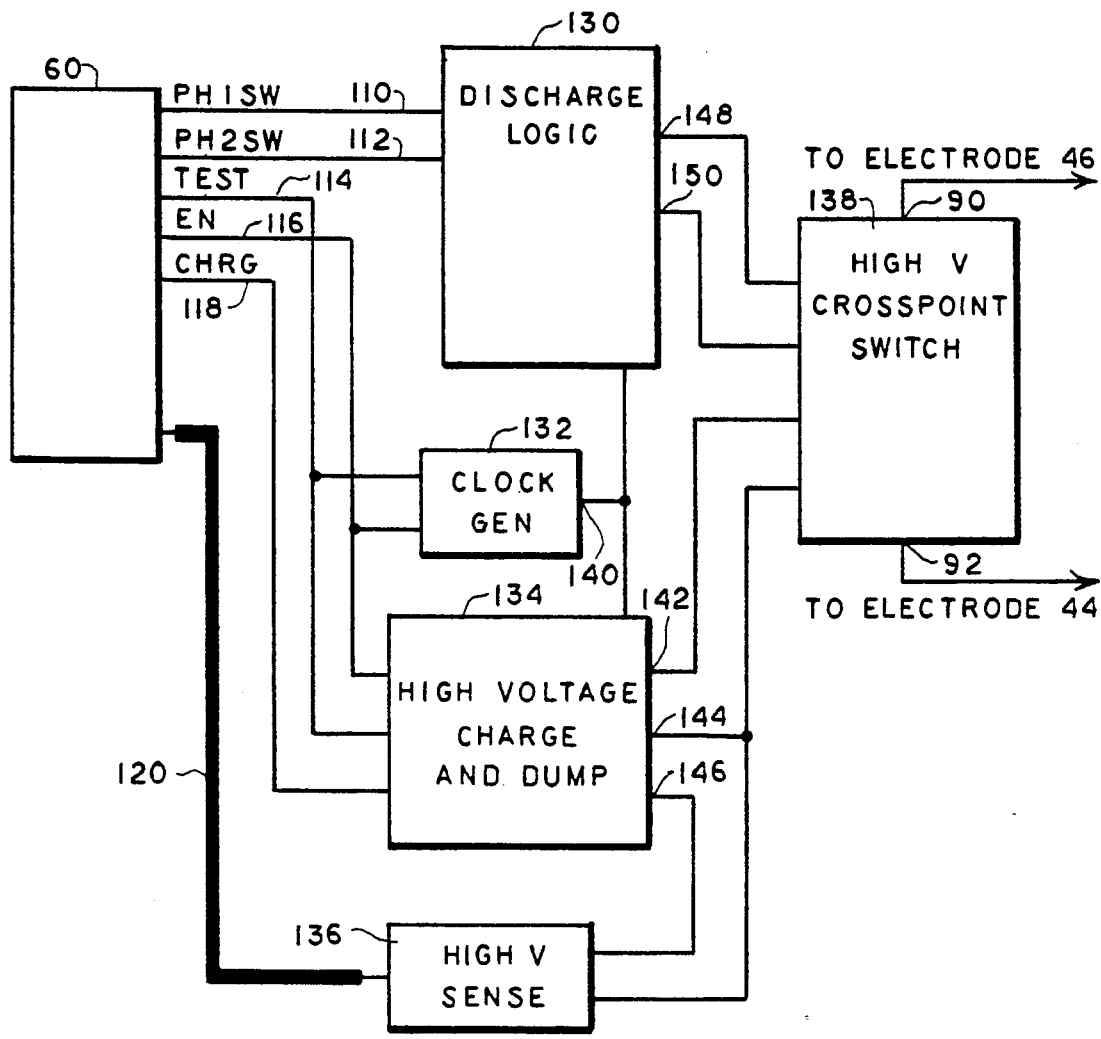
FIG. 2 is a block diagram of the pulse generator of FIG. 1 embodying the present invention.

Referring now to FIG. 2, it illustrates, in block diagram form, the pulse generator 66 of FIG. 1 in conjunction with the microprocessor 60. The pulse generator 66 generally includes discharge logic 130, a clock generator 132, a high voltage charge and dump circuit 134, a high voltage sensing circuit 136, and a crosspoint switch circuit 138.

Control line 118 is coupled to the high voltage charge and dump circuit 134. Control line 116 is coupled to the clock generator 132 and to the high voltage charge and dump circuit 134. Control line 114 is coupled to the clock generator 132 and to the high voltage charge and dump circuit 134. Lastly, control lines 110 and 112 are coupled to the discharge logic 130.

Clock generator 132 includes an output 140 which is coupled to discharge logic 130 and the high voltage charge and dump circuit 134. The high voltage charge and dump circuit 134 includes a first output 142 which is coupled to the high voltage crosspoint switch 138 and a second output 144 which is coupled to the high voltage crosspoint switch circuit 138 and to the high voltage sense circuit 136. The high voltage charge and dump circuit 134 also includes a third output 146 which is coupled to the high voltage sense circuit 136. The second output 144 is coupled to the negative terminal of the storage capacitor and the output 142 is coupled to the positive terminal of the storage capacitor when the aforementioned enable switch is closed by receipt of the enable control signal over line 116. This allows the storage capacitor to be coupled to the high voltage crosspoint switch circuit 138 for application of the cardioverting or defibrillating electrical energy to electrodes 44 and 46 from outputs 90 and 92. The third output 146 is coupled directly to the positive terminal of the storage capacitor. This permits the high voltage sense circuit 136 to sense the voltage of the storage capacitor as the defibrillating or cardioverting electrical energy is stored therein. The voltage across the storage capacitor is digitized by an analog to digital converter within the high voltage sense circuit 136 and the multiple-bit representation of the storage capacitor voltage is provided to the microprocessor 60 over the multiple-bit bus 120. When the microprocessor determines that the storage capacitor is fully charged, the pulse generator 66 is ready to either discharge all of the electrical energy stored in the storage capacitor internally within the pulse generator 66 or to apply the electrical energy stored in the storage capacitor to the high voltage crosspoint switch circuit 138 to be applied to the electrodes 46 and 44 for cardioverting or defibrillating the atria 16 and 18 of the heart 10.

The discharge logic circuit 130 includes a first output 148 and a second output 150. The outputs 148 and 150 are coupled to the high voltage crosspoint switch 138. When the cardioverting or defibrillating electrical energy is applied to the electrodes 46 and 44 during the first phase, the first output 148 of discharge logic 130 is active and during the second phase, output 150 is active. The high voltage crosspoint switch circuit 138 therefore applies the cardioverting or defibrillating electrical energy stored in the storage capacitor of the high voltage charge and dump circuit 134 responsive to the enable control signals provided at outputs 148 and 150 of the discharge logic 130.

For applying the cardioverting or defibrillating electrical energy to the electrodes 46 and 44, the high voltage crosspoint switch circuit 138 includes the aforementioned first pulse generator output 90 and the second pulse generator output 92. As illustrated, these outputs are coupled to the electrodes 46 and 44 respectively.

Figure 3:
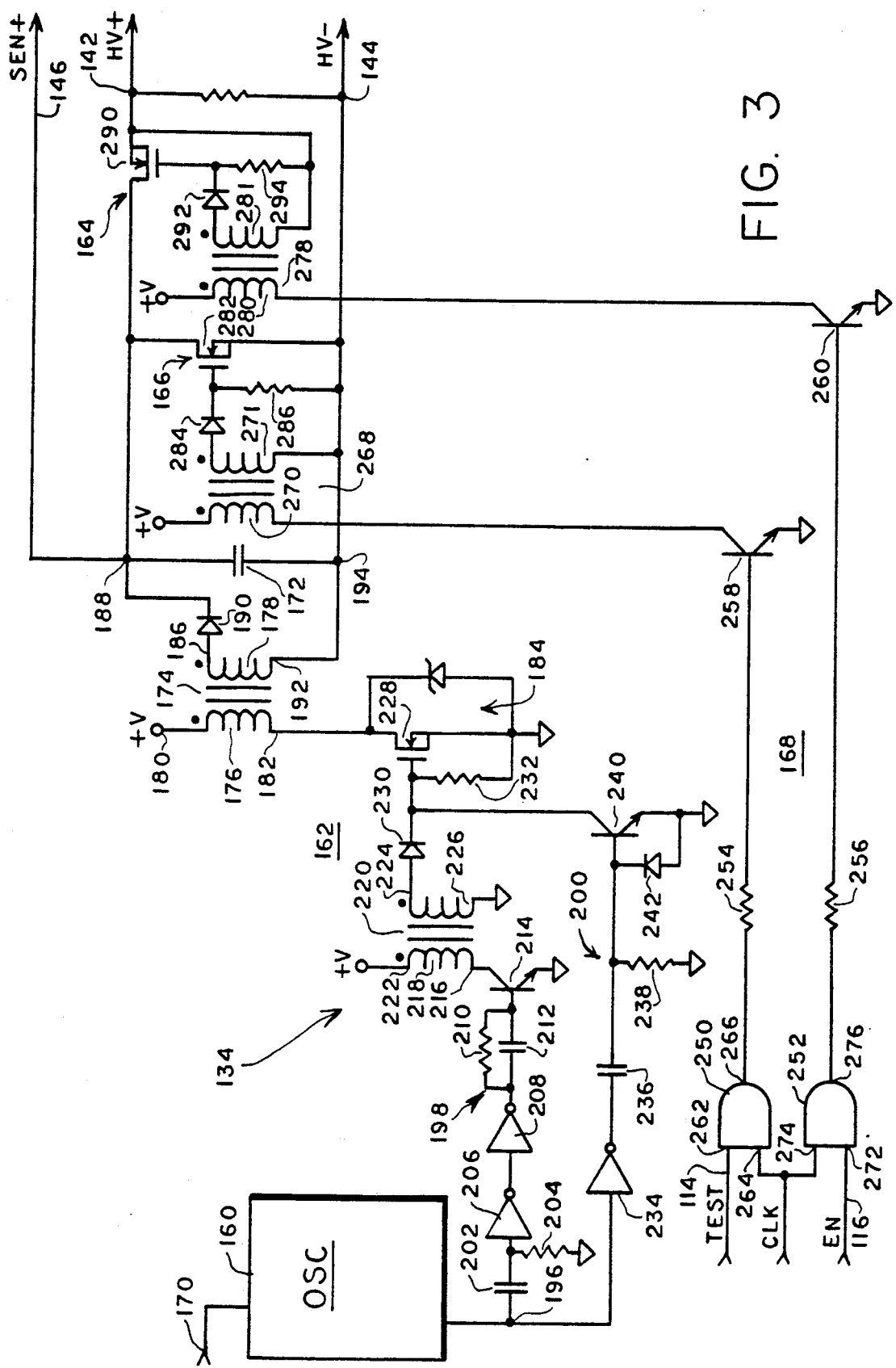
FIG. 3 is a schematic diagram of the high voltage charge and dump circuit of FIG. 2 embodying aspects of the present invention.

Referring now to FIG. 3, it illustrates, in schematic circuit diagram form, the high voltage charge and dump circuit 134 illustrated in FIG. 2 of the pulse generator 66. The high voltage charge and dump circuit 134 generally includes an oscillator 160, a charging circuit 162, an enable switch 164, a test switch 166, and a control signal transfer circuit 168.

The charging circuit 162, responsive to receiving the charge control signal at input 170 over control line 118 (FIG. 2) converts the low voltage of the battery 67 (FIG. 1) to a low duty cycle pulsating high voltage for storing the high voltage electrical energy in the storage capacitor 172. To that end, the charging circuit 162 includes a flyback transformer 174 having a primary 176 and a secondary 178. The primary 176 includes a first terminal 180 coupled to the battery voltage (+V) and second terminal 182 which is coupled to a switch 184. The secondary 178 includes a first terminal 186 which is coupled to the positive terminal 188 of capacitor 172 by a rectifying means in the form of a diode 190. The second terminal 192 of the secondary 178 is coupled to the negative terminal 194 of capacitor 172. As a result, the secondary 178 is coupled across the storage capacitor 172.

When the cardioverting or defibrillating electrical energy is stored within capacitor 172, the switch 184 opens and closes in accordance with a low duty cycle control signal. The low duty cycle control signal may, for example, have a duty cycle less than 50% and preferably less than 30%. Most preferably, the duty cycle of the low duty cycle control signal is on the order of about 8% to 10%. The low duty cycle control signal which is generated, in a manner to be described hereinafter, closes and opens switch 184 to correspondingly couple the second terminal 182 of the primary 176 of flyback transformer 174 to common potential. The frequency of the low duty cycle control signal may be on the order of 10 kilohertz so that for each 100 microsecond period, the switch 184 is closed for 10 microseconds and opened for 90 microseconds. The closing and opening of the switch 184 induces a periodic voltage across transformer secondary 178 which is rectified by diode 190 to a pulsating voltage applied to capacitor 172 for charging capacitor 172 and storing the cardioverting or defibrillating electrical energy therein. This charging of capacitor 172 causes the voltage on capacitor 172 to increase.

The low duty cycle control signal is provided by the oscillator 160. Such oscillators are well known in the art. The oscillator 160 includes an output 196 which is coupled to the switch 184 through a first means 198 which causes the switch 184 to close and a second means 200 which causes the switch 184 to open.

The first means 198 includes a coupling capacitor 202, a resistor 204, a pair of series coupled inverters 206 and 208, and resistor 210 and capacitor 212 coupled in parallel. The common junction of resistor 210 and capacitor 212 is coupled to the base of a bipolar NPN transistor 214. The emitter of transistor 214 is coupled to ground and the collector of transistor 214 is coupled to the second terminal 216 of a primary winding 218 of a coupling transformer 220. The transformer 220 includes a first primary terminal 222 which is coupled to a battery voltage (+V). Transformer 220 includes a secondary having a first terminal 224 and a second terminal 226.

The switch 184 is in the form of an N-channel field-effect transistor 228. The gate of transistor 228 is coupled to the first terminal 224 of the secondary of transformer 220 by a rectifying means in the form of a diode 230. The source of transistor 228 is coupled to common potential and to the gate of transistor 228 by a resistor 232. The drain of transistor 228 is coupled to the second terminal 182 of the primary 176 of the flyback transformer 174.

The second means 200 includes an inverter 234, a capacitor 236, a resistor 238, and a bipolar NPN transistor 240. The collector of transistor 240 is coupled to the gate of the N-channel field effect transistor 228 and the emitter of transistor 240 is coupled to common potential. The emitter is also coupled to the base of transistor 240 by a diode 242.

When the output of oscillator 160 is at a high level for 10 microseconds, this high level is conducted through the first means 198 to turn transistor 214 on. This causes coupling transformer 220 to induce a voltage across its secondary which is rectified by diode 230 to turn field-effect transistor 228 on and to thus couple the second terminal 182 of primary 176 of flyback transformer 174 to ground. When the trailing edge of the 10 microsecond high level of oscillator 160 occurs and the oscillator output goes low, transistor 240 is turned on to couple the gate of field-effect transistor 228 to common potential. This forces transistor 228 off. Transistor 228 will remain off for a period of 90 microseconds. Hence, the leading edge of the positive going oscillator output is conveyed through the first means 198 to turn transistor 228 on and the trailing edge is conveyed through the second means 200 to turn transistor 240 on to in turn force transistor 228 off. The foregoing low duty cycle control signal causes the flyback transformer 174 to convert the low battery voltage to a pulsating, low duty cycle, high voltage which is rectified by diode 190 and applied to capacitor 172 for storing the cardioverting or defibrillating electrical energy in the storage capacitor 172.

By virtue of the low duty cycle of the control signal, the capacitor 172 is slowly charged to its fully charged condition. For example, with the battery voltage being 3 volts, and the final charge voltage of the capacitor being on the order of 350 volts, and with the duty cycle of the control signal being approximately 10%, the time to charge the storage capacitor 172 is preferably on the order of seconds, and most preferably greater than about 60 seconds. Such slow charging of the storage capacitor 172 minimizes the effect of the battery's internal impedance and therefore prolongs the useful life of the battery powering the atrial defibrillator by allowing more efficient use of battery energy. More specifically, by virtue of the slow charging of the capacitor 172, the number of times in which the capacitor 172 may be charged for cardioverting or defibrillating the atria of the heart is substantially increased over prior art arrangements wherein such storage capacitors were quickly charged.

The control signal conveying circuit 168 of the high voltage charge and dump circuit 134 includes a first AND gate 250, a second AND gate 252, a resistor 254, another resistor 256, a bipolar transistor 258, and another bipolar transistor 260. AND gate 250 includes a first input 262 which is coupled to the test control line 114 and a second input 264 which is coupled to the output 140 of the clock generator 132 of FIG. 2. AND gate 250 also includes an output 266 which is coupled to the base of transistor 258 through the resistor 254. Transistor 258 includes an emitter which is coupled to common potential and a collector which is coupled to one end of a primary winding 270 of a coupling transformer 268. The other end of primary winding 270 is coupled to battery potential (+V).

Similarly, AND gate 252 includes a first input 272 which is coupled to the enable control line 116 and a second input 274 which is coupled to the output 140 of the clock generator 132 of FIG. 2. AND gate 252 also includes an output 276 which is coupled to the base of transistor 260 through resistor 256. Transistor 260 includes an emitter which is coupled to common potential and a collector which is coupled to one end of a primary winding 280 of another coupling transformer 278. The other end of primary winding 280 is coupled to a battery potential (+V).

When the charging of storage capacitor 172 is completed, the microprocessor provides either a test control signal over line 114 or an enable control signal over line 116. The test control signal 114 ultimately results in all of the electrical energy stored in storage capacitor 172 to be discharged internally within the high voltage charge and dump circuit 134 in a manner to be described hereinafter. The enable control signal conveyed over line 116 ultimately results in the capacitor 172 being coupled to the crosspoint switch 138 of FIG. 2 to be described hereinafter to enable the cardioverting or defibrillating electrical energy stored in storage capacitor 172 to be applied to electrodes 46 and 44 of lead 36 for cardioverting or defibrillating the atria of the heart. The test control signal and enable control signal issued by the microprocessor 60 are steady state constant level control signals. The clock generator 132 of FIG. 2 is responsive to receiving either the enable control signal or the test control signal for generating a periodic or toggling output which is received at input 264 of AND gate 150 and input 274 of AND gate 252. Since the test and enable control signals activate the clock generator, the test control signal or the enable control signal will already be present at the control signal conveying circuit 168 when the output of clock generator 132 is applied to AND gates 250 and 252. As a result, AND gate 250 converts the constant level test control signal to a time varying periodic test control signal and AND gate 252 converts the constant level enable control signal to a time varying periodic enable control signal.

When the microprocessor issues the test control signal, the periodic test control signal generated at output 266 of AND gate 250 is conveyed to the base of transistor 258. This causes transistor 258 to turn on and off to provide a periodic voltage across primary 270 of isolation or coupling transformer 268. This in turn induces a voltage across the secondary 271 of coupling transformer 268. The test switch 166 takes the form of an N channel field effect transistor 282. The gate of transistor 282 is coupled to the secondary 271 of coupling transformer 268 by a rectifying means or diode 284. The diode 28 rectifies the periodic test control signal coupled across transformer 268 to turn transistor 282 on. As will be noted, transistor 282 is coupled across capacitor 172. As a result, when transistor 282 is turned on, the electrical energy stored in capacitor 172 is discharged through transistor 282 internally within the high voltage charge and dump circuit 134. A resistor 286, which is coupled across the gate and source of transistor 282, turns transistor 282 off when the test control signal is terminated.

AND gate 252 converts the constant level enable control signal received from line 116 to a time varying periodic enable control signal in a similar manner. It provides the periodic enable control signal at output 276 which is applied to the base of transistor 260. This turns the transistor 260 on and off for conveying the periodic enable control signal to the primary 280 of isolation or coupling transformer 278. This in turn induces a periodic enable control signal across the secondary 281 of coupling transformer 278. The enable switch 164 takes the form of an N-channel field effect transistor 290. The gate of field-effect transistor 290 is coupled to the secondary 281 of coupling transformer 278 by a rectifying means or diode 292 which rectifies the periodic enable control signal for turning on transistor 290. As will be noted in the Figure, transistor 290 is coupled in series with the positive terminal 188 of capacitor 172. As a result, when transistor 290 is turned on by the enable control signal, the capacitor 172 is coupled across outputs 142 and 144 of the high voltage charge and dump circuit 134 for coupling capacitor 172 to the crosspoint switch circuit 138 of FIG. 2. A resistor 294, which is coupled across the gate and source of transistor 290, turns transistor 290 off when the enable control signal is terminated.

Figure 4:
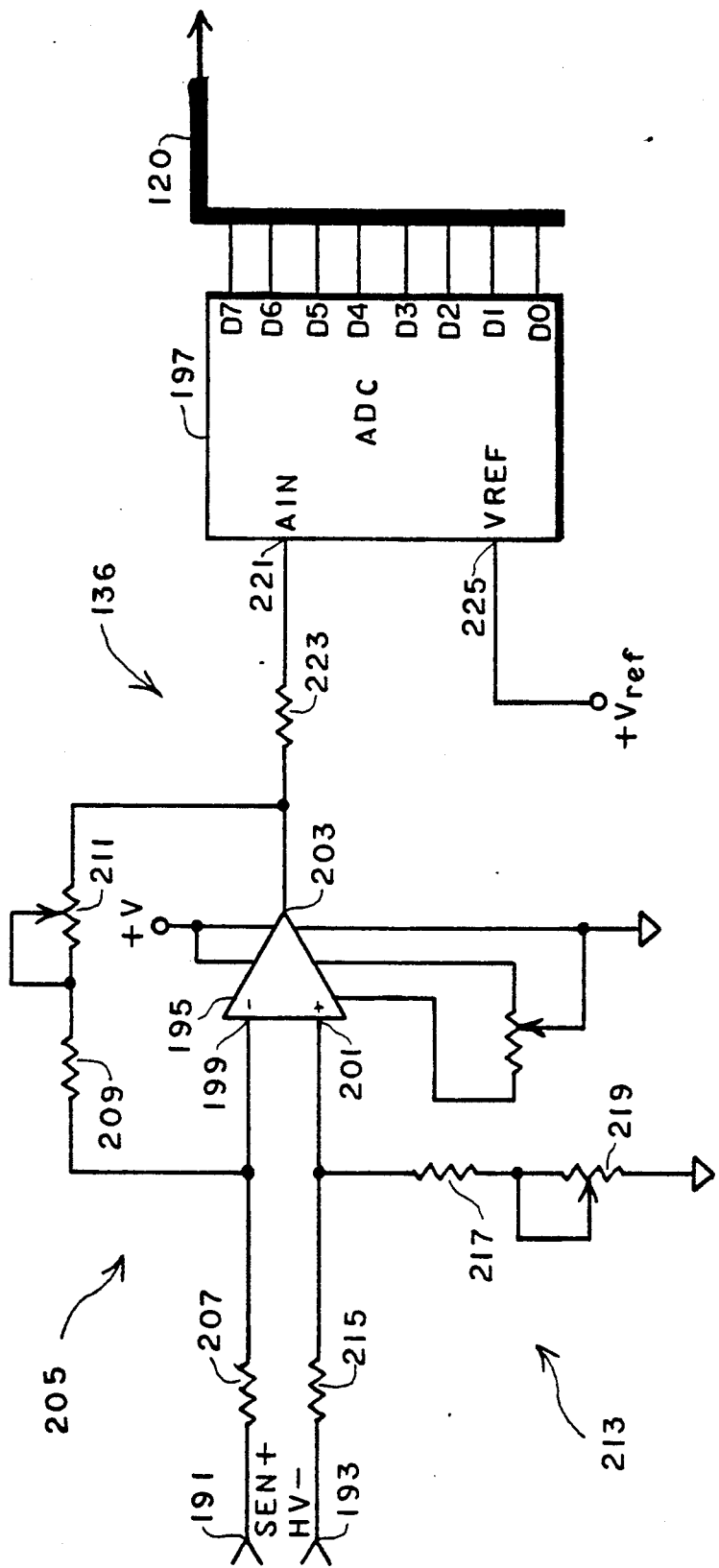
FIG. 4 is a schematic diagram of the high voltage sense circuit if FIG. 2 embodying additional aspects of the present invention.

Referring now to FIG. 4, it illustrates, in schematic circuit diagram form, the high voltage sense circuit 136 of FIG. 2. Output 146 and output 144 are coupled across capacitor 172 and to the high voltage sense circuit 136 at inputs 191 and 193 respectively to provide the high voltage sense circuit 136 with the present voltage of capacitor 172. The high voltage sense circuit 136 includes an amplifier 195 and an analog to digital converter 197. The amplifier 195 includes inputs 199 and 201 and an output 203. Input 199 is coupled to input 191 by a first voltage divider 205 including resistor 207 coupled between input 199 and input 191 and the series combination of fixed resistor 209 and variable resistor 211 coupled between input 199 and output 203. Similarly, input 201 is coupled to input 192 by a second voltage divider 213 including resistor 215 coupled between input 201 and input 193 and the series combination of fixed resistor 217 and variable resistor 219 coupled between input 201 and common potential.

The first and second voltage dividers 205 and 213 provide two important functions. First, the voltage dividers provide the low voltage circuitry, such as amplifier 195 and analog to digital converter 19 with isolation protection from the high voltage across capacitor 172 to protect such low voltage circuitry from damage. Second, the voltage dividers provide scaling of the voltage across capacitor 172 for use by the amplifier 195. Third, the voltage dividers prevent currents from flowing through sensing leads, and through the case of the device into the body. Preferably, the values of the resistors forming the first and second voltage dividers are selected to provide a scaling factor of about two hundred to one with resistor 207 and 215 being on the order of 50 megohms.

The output 203 of amplifier 195 is coupled to an input 221 of analog to digital converter 197 by a resistor 223. A reference input 225 of analog to digital converter 197 is coupled to a precision voltage reference.

The analog to digital converter 197 digitizes the output of amplifier 195 and conveys an 8-bit digital representation of the capacitor voltage over the multiple-bit bus 120 to the microprocessor 60. This permits the microprocessor 60 to sense the voltage of capacitor 172 and to terminate the charging of capacitor 172 when the capacitor 172 is fully charged.

Figure 5:
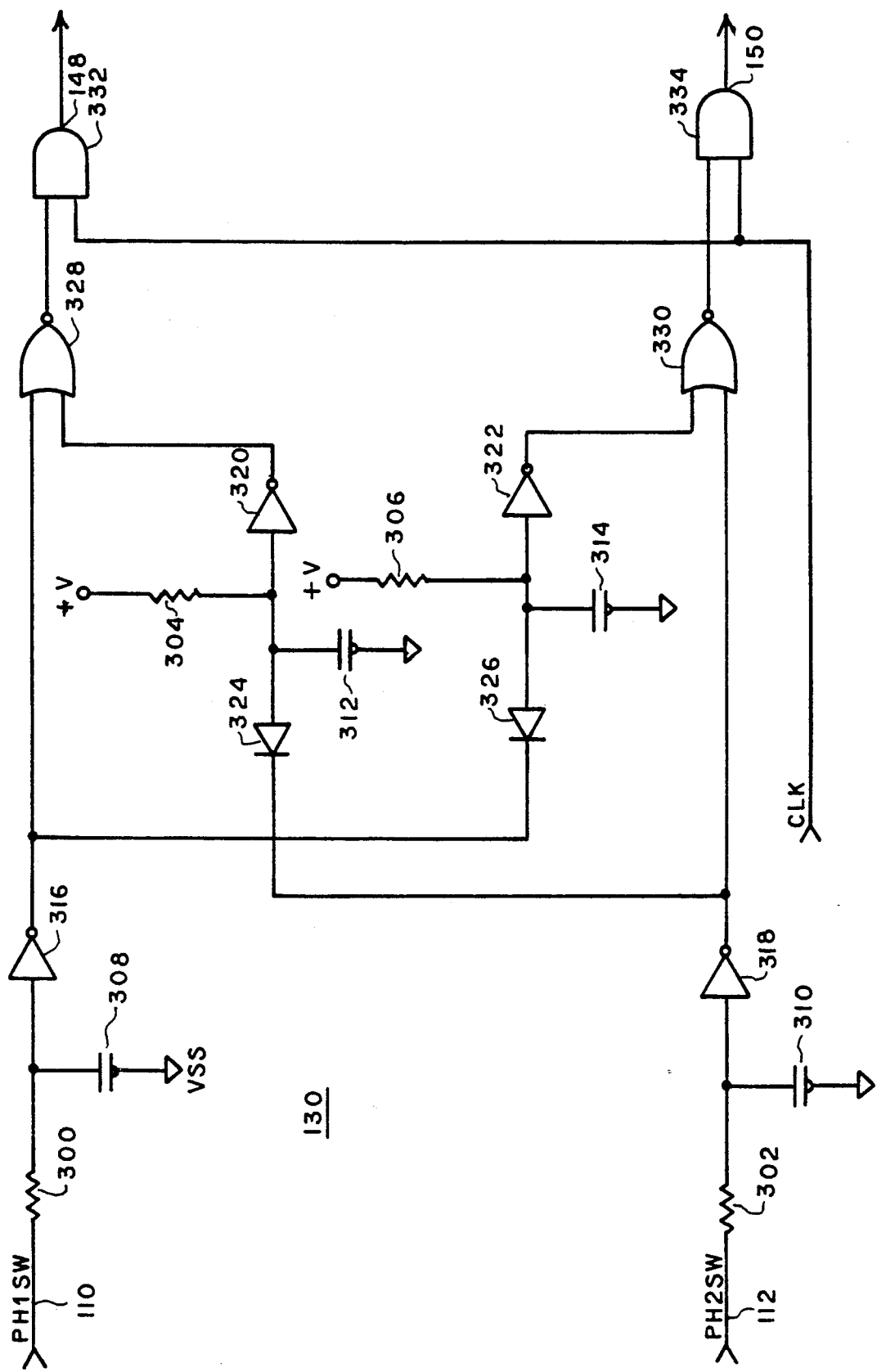
FIG. 5 is a schematic diagram of the discharge control logic of FIG. 2.

Referring now to FIG. 5, it illustrates, in schematic circuit diagram form, the discharge logic circuit 130 of FIG. 2. As previously mentioned, when the cardioverting or defibrillating electrical energy is applied to the atria of the heart through the lead 36 and electrodes 46 and 44, the electrical energy is preferably applied with a biphasic waveform wherein electrode 46 is positive with respect to electrode 44 during a first phase and electrode 44 is positive with respect to electrode 46 during an immediately following second phase. Preferably, the first and second phases are equal in duration of 3 milliseconds. Hence, when the cardioverting or defibrillating electrical energy is applied to electrodes 46 and 44 for cardioverting or defibrillating the atria of the heart, the microprocessor first issues a constant level phase one control signal over line 110 and then a constant level phase two control signal over line 112. When the phase one control signal is applied, it is a high level, and the phase two control signal is a low level. Conversely, when the phase two control signal is applied, the phase two control signal is a high level and the phase one control signal is a low level. The discharge control logic 130 of FIG. 5 converts the constant level phase one and phase two control signals to time varying periodic phase one and phase two drive signals for controlling the crosspoint switch circuit 138 of FIG. 2 in a manner to be described hereinafter.

The discharge control logic circuit 130 includes resistors 300, 302, 304, and 306, capacitors 308, 310, 312, and 314, and inverters 316, 318, 320, and 322. The discharge control logic circuit 130 further includes diodes 324 and 326, NOR gates 328 and 330, and AND gates 332 and 334. The input of inverter 316 is coupled to the control line 110 by resistor 300 and to common potential by capacitor 308. The output of inverter 316 is coupled to a first input of NOR gate 328. NOR gate 328 includes an output which is coupled to a first input of AND gate 332.

Similarly, the input of inverter 318 is coupled to control line 112 through resistor 302 and to common potential by capacitor 310. The output of inverter 318 is coupled to a first input of NOR gate 330. The output of NOR gate 330 is coupled to a first input AND gate 334.

The input of inverter 320 is coupled to the battery voltage (+V) by resistor 304 and to common potential by capacitor 312. The common junction of resistor 304 and capacitor 312 is also coupled to the output of inverter 318 and the first input of NOR gate 330 by diode 324. The output of inverter 320 is coupled to the second input of NOR gate 328.

The input of inverter 322 is coupled to battery voltage (+V) by resistor 306 and to common potential by capacitor 314. The common junction of resistor 306 and capacitor 314 is coupled to the output of inverter 316 and to the first input of NOR gate 328 by diode 326. The output of inverter 322 is coupled to the second input of NOR gate 330.

AND gate 332 includes a second input which is coupled to the output 140 of clock generator 132 of FIG. 2. Similarly, AND gate 334 includes a second input which is coupled to the output 140 of clock generator 132 of FIG. 2. Lastly, the output of AND gate 332 forms the output 148 of the discharge control logic circuit 130 and the output of AND gate 334 forms the output 150 of the discharge control logic circuit 130.

As previously described, during the application of the cardioverting or defibrillating electrical energy to the atria of the heart, the enable control signal is provided by the microprocessor for coupling the storage capacitor to the crosspoint switch circuit 138. The enable control signal causes the clock generator 132 to provide clock pulses which, in addition to being provided to the high voltage charge and dump circuit 134, are also provided to the discharge control logic circuit 130 at the second inputs of AND gates 332 and 334. During the first phase of the cardioversion or defibrillation, the phase one control signal on line 110 is a constant high level and the phase two control signal on line 112 is a constant low signal. When the first phase control signal is asserted, the output 148 of the discharge control logic circuit 130 provides the periodic phase one drive control signal. During the second phase, when the phase two control signal on line 112 is a constant high level and the phase one control signal on line 110 is a constant low level, output 150 provides the periodic phase two drive control signal. As will be seen hereinafter, the phase one and phase two periodic drive control signals control the crosspoint switch circuit 138 which will now be described in detail.

Figure 6:
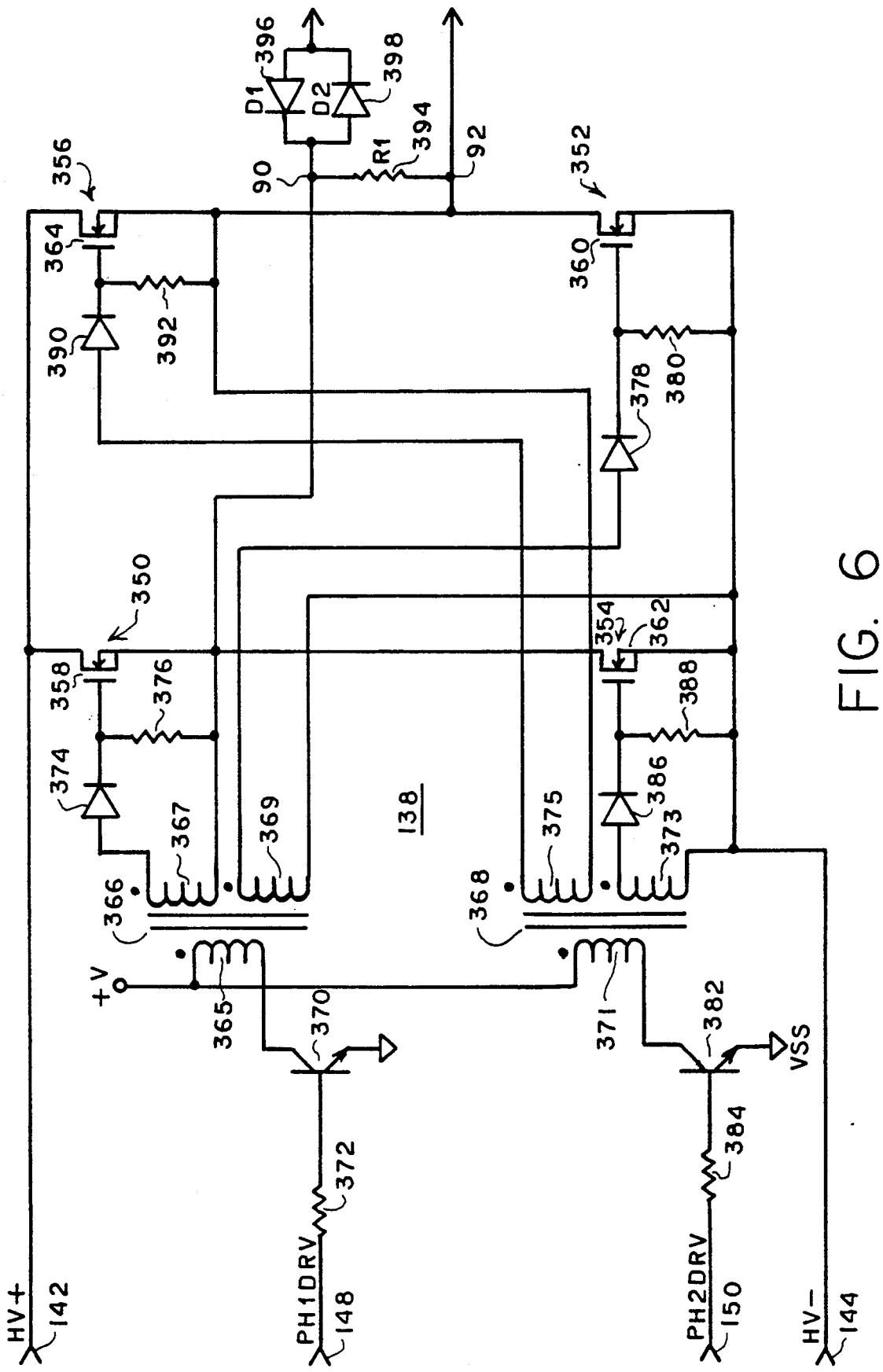
FIG. 6 is a schematic diagram of the crosspoint switch circuit of FIG. 2 embodying further aspects of the present invention.

Referring now to FIG. 6, it illustrates, in schematic circuit diagram form, the high voltage crosspoint switch circuit 138 illustrated in FIG. 2. The crosspoint switch circuit 138 generally includes a first switch 350, a second switch 352, a third switch 354, and a fourth switch 356. The switches 350, 352, 354, and 356 preferably take the form of N-channel field-effect transistors 358, 360, 362, and 364 respectively. The high voltage crosspoint switch circuit 138 further includes a first isolation or coupling transformer 366 and a second isolation or coupling transformer 368.

The drains of transistors 358 and 364 are coupled to the output 142 of the high voltage charge and dump circuit 134. The sources of transistors 360 and 362 are coupled to the output 144 of the high voltage charge and dump circuit 134. The source of transistor 358 and the drain of transistor 362 are coupled to the output 90 of the high voltage crosspoint switch circuit 138. The source of transistor 364 and the drain of transistor 360 are coupled to the output 92 of the high voltage crosspoint switch circuit 138. As a result, when the enable switch transistor 290 of the high voltage charge and dump circuit 134 is turned on, transistor 358 is coupled between the positive terminal of capacitor 172 and output 90 and transistor 364 is coupled between the positive terminal of capacitor 172 and output 92. Transistor 360 is coupled between the negative terminal of capacitor 172 and output 92 and transistor 362 is coupled between the negative terminal of capacitor 172 and output 90.

The first coupling transformer 366 couples the periodic phase one drive control signal to transistors 358 and 360. To that end, coupling transformer 366 includes a primary 365 having a first end coupled to the battery voltage (+V) and a second end coupled to the collector of bipolar transistor 370. Transistor 370 has an emitter coupled to common potential and a base coupled to output 148 of the discharge control logic circuit 130 through resistor 372 for receiving the periodic phase one drive control signal. The coupling transformer 366 also includes a pair of secondary windings including a first secondary winding 367 and second secondary winding 369. The first secondary winding includes a first end or terminal which is coupled to the gate of transistor 358 through a rectifying means or diode 374. The second end or terminal of winding 367 is coupled to the source of transistor 358. The gate and source of transistor 358 are coupled together by a resistor 376.

The second secondary winding 369 includes a first end or terminal which is coupled to the gate of transistor 360 by another rectifying means or diode 378. The second end or terminal of secondary winding 369 is coupled to the source of transistor 360. The gate and source of transistor 360 are coupled together by a resistor 380.

The second coupling transformer 368 couples the periodic phase two drive control signal to transistors 362 and 364. To that end, the second coupling transistor 368 includes a primary 371 having a first end or terminal coupled to battery voltage (+V) and a second end or terminal coupled to the collector of another bipolar transistor 382. Transistor 382 has an emitter coupled to common potential and a base coupled to the output 150 of the discharge control logic circuit 130 by a resistor 384. The second coupling transformer 368 further includes a first secondary winding 373 and a second secondary winding 375. The first secondary winding 373 has a first end which is coupled to the gate of transistor 362 by another rectifying means or diode 386. The second end or terminal of winding 373 is coupled to the source of transistor 362. The gate and source of transistor 362 are coupled together by a resistor 388.

The second secondary winding 375 includes a first end or terminal which is coupled to the gate of transistor 364 by another rectifying means or diode 390. The second end of winding 375 is coupled to the source of transistor 364. The gate and source of transistor 364 are coupled together by a resistor 392.

As will be further noted in FIG. 6, a resistor 394 is coupled across outputs 90 and 92 of the high voltage crosspoint switch circuit 138. Also, a pair of diodes 396 and 398 are coupled in antiparallel relation with the cathode of diode 396 being coupled to the anode of diode 398 and the cathode of diode 398 being coupled to the anode of diode 396. The common junction of the cathode of diode 396 and the anode of diode 398 is coupled to output 90 and the common junction of the anode of diode 396 and the cathode of diode 398 are coupled to electrode 46 of lead 36. The antiparallel diodes 396 and 398 together with resistor 394 eliminate leakage currents to the electrodes 46 and 44 of lead 36. In addition, the diodes 396 and 398 and resistor 394 serve to block low voltages which may be present at the field-effect transistor switches during test operations of the storage capacitor 172 from reaching the electrodes 46 and 44.

During phase one of the cardioversion or defibrillation, the periodic phase one drive control signal drives transistor 370 on and off. This transfers the phase one drive control signal to the primary 365 of the first coupling transformer 366. The periodic phase one drive control signals are induced across the secondary windings 367 and 369. The diodes 374 and 378 rectify the induced control signals and turn on field-effect transistors 358 and 360. This applies the positive terminal of capacitor 172 to output 90 and the negative terminal of capacitor 172 to output 92.

During phase two of the cardioversion or defibrillation, the periodic phase two drive control signal drives transistor 382 on and off to transfer the drive two control signal to primary 371 of the second coupling transformer 368. The periodic phase two drive control signal is thus induced across the secondary 373 and 375 of the second coupling transformer 368. The diodes 386 and 390 rectify the phase two drive control signals to turn on transistors 362 and 364. As a result, the positive terminal of the capacitor 172 is coupled to output 92 and the negative terminal of capacitor 172 is coupled to output 90. Resistors 376 and 380 turn transistors 358 and 360 off when the phase one drive control signal is terminated and resistors 388 and 392 turn off transistors 36 and 364 when the phase two drive control signal is terminated.

As will be noted from the foregoing, transformer coupling of the control signals is utilized for the enable control signal, the test control signal, the phase one control signal, and the phase two control signal. Such transformer coupling together with the rectifying diodes for turning respective field-effect transistor switches on and off are preferably utilized to reduce parts count in the resulting atrial defibrillator. The internal capacitance of the respective field-effect transistor switches is utilized as the filter capacitance in conjunction with the corresponding diodes. The foregoing hence reduces circuitry complexity with the resulting advantage of high reliability.

In operation, and making reference to FIGS. 1 and 2, sense amplifiers 50 and 54 and R wave detectors 52 and 56 continuously detect for electrical activations (R waves) of the heart 10. When the intervals between the R waves determined by the microprocessor 60 indicate that atrial fibrillation may be present, the microprocessor 60 activates sense amplifier 58. Atrial activity of the heart 10 is then monitored. If the microprocessor 60 determines that atrial fibrillation is present, it issues the charge control signal on line 118 to cause the high voltage charge and dump circuit 134 to charge the storage capacitor 172 (FIG. 3). In doing so, the charging circuit is activated and the low duty cycle high frequency signal is applied to the flyback transformer 176 (FIG. 3) for charging the storage capacitor 172. By virtue of the low duty cycle of the charging voltage, the capacitor 172 is slowly charged and will achieve a full charge of, for example, 350 volts, in about one minute. This slow charging of the storage capacitor 172 by virtue of the low duty cycle causes a low average current drain on the battery 67 of the implanted atrial defibrillator 30. This allows the use of present battery technologies which possess demonstrated long shelf life but which have been unsuitable for use in prior defibrillators such as ventricular defibrillators. Such a battery may be, for example, a lithium silicon vanadium oxide battery capable of providing three volts at 15 milliamperes.

As the capacitor 172 is charged, the high voltage sense circuit 136 (FIG. 4) continuously converts the storage capacitor voltage to a multiple-bit representation, for example, 8-bits, and conveys the multiple-bit representation of the capacitor voltage to the microprocessor over the multiple-bit bus 120. When the charging of the storage capacitor is completed, the microprocessor provides the enable control signal on line 116. This causes the high voltage charge and dump circuit 134 to couple the storage capacitor 172 across the high voltage crosspoint switch circuit 138.

With the storage capacitor 172 is coupled across the high voltage crosspoint switch circuit 138, the microprocessor then, in synchronism with a detected R wave, issues the phase one control signal. The discharge logic circuit 130 converts the constant level phase one control circuit to the periodic phase one control signal to cause the high voltage crosspoint switch circuit 138 to apply the positive terminal of capacitor 172 to output 90 and thus electrode 46 and the negative terminal of capacitor 172 to output 92 and thus electrode 44. As previously described, phase one preferably lasts three milliseconds.

Following phase one, the microprocessor issues the constant level phase two control signal. This causes the discharge logic circuit 130 to provide the high voltage crosspoint switch circuit 138 with the periodic phase two control signal. This causes the high voltage crosspoint switch circuit 138 to apply the positive terminal of capacitor 172 to output 92 and thus electrode 44 and the negative terminal of capacitor 172 to output 90 and thus electrode 46. As previously described, phase two preferably lasts three milliseconds.

Upon completion of phase two, the enable control signal and the phase two control signal are terminated. The sense amplifiers 50 and 54 and the R wave detectors 52 and 56 once again monitor electrical activations (R waves) of the heart to enable the microprocessor to determine if the atrial fibrillation has been arrested. If atrial fibrillation should persist, the foregoing operation is repeated.

While a particular embodiment of the present invention has been shown and described, modifications may be made, and it is therefore intended to cover in the appended claims all such changes and modifications which fall within the true spirit and scope of the invention.

What is claimed is:

1. A pulse generator for use in an implantable atrial defibrillator for providing cardioverting electrical energy to the atria of a heart through lead means associated with the atria of the heart, said pulse generator comprising:
    a depletable, low-voltage, power source;
    oscillator means for generating a low duty cycle control voltage;
    charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor; and
    switch means for selectively coupling said storage capacitor means to said lead means for applying a portion of said stored electrical energy to the atria of the heart through said lead means for cardioverting the atria of the heart.

2. A pulse generator as defined in claim 1 wherein said charging circuit further includes enable switch means responsive to an enable control signal for coupling said storage capacitor means to said switch means.

3. A pulse generator for use in an implantable atrial defibrillator for providing cardioverting electrical energy to the atria of the heart through lead means associated with the atria of the heart, said pulse generator comprising:
    a depletable, low voltage, power source;
    oscillator means for generating a low duty cycle control voltage;
    charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor; and
    switch means for selectively coupling said storage capacitor means to said lead means for applying a portion of said stored electrical energy to the atria of the heart through said lead means for cardioverting the atria of the heart,
    said charging circuit further including enable switch means responsive to an enable control signal for coupling said storage capacitor means to said switch means and isolation means for coupling said enable control signal to said enable switch means.

4. A pulse generator as defined in claim 3 wherein said isolation means comprises transformer means.

5. A pulse generator as defined in claim 4 wherein said enable switch means comprises a field-effect transistor having a gate coupled to said transformer means for receiving said enable control signal.

6. A pulse generator as defined in claim 5 wherein said enable control signal has a time varying waveform and wherein said charging circuit further includes rectifying means coupling said transformer means to said field-effect transistor gate for rectifying said enable control signal.

7. A pulse generator as defined in claim 6 wherein said rectifying means comprises a diode.

8. A pulse generator a defined in claim 7 wherein said charging circuit further includes isolation means for coupling said test control signal to said test means.

9. A pulse generator as defined in claim 8 wherein said isolation means comprises transformer means.

10. A pulse generator as defined in claim 9 wherein said test means includes a field-effect transistor having a gate coupled to said transformer means for receiving said control signal.

11. A pulse generator as defined in claim 10 wherein said test control signal has a time varying waveform and wherein said charging circuit further includes rectifying means coupling said transformer means to said field-effect transistor gate for rectifying said test control signal.

12. A pulse generator as defined in claim 11 wherein said rectifying means comprises a diode.

13. A pulse generator as defined in claim 1 wherein said switch means are responsive to a first control signal for coupling said storage capacitor means to said lead means with a first polarity and responsive to a second control signal for coupling said storage capacitor means to said lead means with a second polarity opposite said first polarity for applying said portion of said stored energy to the atria of the heart with a biphasic waveform.

14. A pulse generator as defined in claim 13 wherein said storage capacitor means includes a positive terminal and a negative terminal, wherein said lead means includes first and second electrodes, and wherein said switch means comprises a first switch coupled between said positive terminal and said first electrode, a second switch coupled between said negative terminal and said second electrode, a third switch coupled between said negative terminal and said first electrode, and a fourth switch coupled between said positive terminal and said second electrode, said first and second switches closing responsive to said first control signal and said third and fourth switches closing responsive to said second control signal.

15. A pulse generator as defined in claim 1 wherein the duty cycle of said low duty cycle control voltage is then than fifty percent.

16. A pulse generator as defined in claim 15 wherein said duty cycle is equal to or less than thirty percent.

17. A pulse generator for use in an implantable atrial defibrillator for providing cardioverting electrical energy to the atria of a heart through lead means associated with the atria of the heart, said pulse generator comprising:
 a depletable, low voltage, power source;
 oscillator means for generating a low duty cycle control voltage;
 charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor, said charging circuit including test means coupled across said storage capacitor and responsive to a test control signal for discharging all of said stored electrical energy; and
 switch means for selectively coupling said storage capacitor means to said lead means for applying a portion of said stored electrical energy to the atria of the heart through said lead means for cardioverting the atria of the heart.

18. A pulse generator for use in an implantable atrial defibrillator for providing cardioverting electrical energy to the atria of the heart through lead means associated with the atria of the heart having first and second electrodes, said pulse generator comprising:
 a depletable, low voltage, power source;
 oscillator means for generating a low duty cycle control voltage;
 charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor;
 switch means for selectively coupling said storage capacitor means to said lead means for applying a portion of said stored electrical energy to the atria of the heart through said lead means for cardioverting the atria of the heart, said switch means being responsive to a first control signal for coupling said storage capacitor means to said lead means with a first polarity and responsive to a second control signal for coupling said storage capacitor means to said lead means with a second polarity opposite said first polarity for applying said portion of said stored energy to the atria of the heart with a biphasic waveform, said switch means comprising a first switch coupled between said positive terminal and said first electrode, a second switch coupled between said negative terminal and said second electrode, a third switch coupled between said negative terminal and said first electrode, and a fourth switch coupled between said positive terminal and said second electrode, said first and second switches closing responsive to said first control signal and said third and fourth switches closing responsive to said second control signal; and
 isolation means for coupling said first control signal to said first and second switches for coupling said second control signal to said third and fourth switches.

19. A pulse generator as defined in claim 18 wherein said first, second, third, and fourth switches each comprise a field-effect transistor.

20. A pulse generator as defined in claim 18 wherein said isolation means comprises a first transformer including a primary for receiving said first control signal, a first secondary coupled to said first switch and a second secondary coupled to said second switch and wherein said isolation means further includes a second transformer including a primary for receiving said second control signal, a first secondary coupled to said third switch, and a second secondary coupled to said fourth switch.

21. A pulse generator as defined in claim 20 wherein said first and second control signals have time varying waveforms and wherein said switch means includes first rectifying means coupling said first transformer first secondary to said first switch, second rectifying means coupling said first transformer second secondary to said second switch, third rectifying means coupling said second transformer first secondary to said third switch, and fourth rectifying means coupling said second transformer second secondary to said fourth switch, said first and second rectifying means rectifying said first control signal and said third and fourth rectifying means rectifying said second control signal.

22. A pulse generator as defined in claim 21 wherein each said first, second, third, and fourth rectifying means comprises a diode.

23. A pulse generator for use in an implantable atrial defibrillator for providing cardioverting electrical energy to the atria of a heart through lead means associated with the atria of the heart including first and second electrodes, said pulse generator comprising:
 a depletable, low voltage, power source;
 oscillator means for generating a low duty cycle control voltage;
 charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor; and
 switch means for selectively coupling said storage capacitor means to said lead means for applying a portion of said stored electrical energy to the atria of the heart through said lead means for cardioverting the atria of the heart, said switch means including a first output and a second output, said second output being coupled to said second electrode and wherein said switch means includes a resistor coupled across said first and second outputs and a pair of anti-parallel diodes coupling at least one of said outputs to one of said electrodes.

24. A pulse generator for use in an implantable atrial defibrillator for providing cardioverting electrical energy to the atria of a heart through lead means associated with the atria of the heart, said pulse generator comprising:

a depletable, low voltage, power source;
oscillator means for generating a low duty cycle control voltage;
charging means coupled to said power source, said charging means including storage capacitor means for storing electrical energy and a charging circuit having a flyback transformer responsive to said low duty cycle control voltage for converting said power source low voltage to pulsating high voltage electrical energy and applying said pulsating high voltage electrical energy to said storage capacitor means for storing electrical energy in said storage capacitor; and
switch means for selectively coupling said storage capacitor means to said lead means for applying a portion of said stored electrical energy to the atria of the heart through said lead means for cardioverting the atria of the heart.

25. A pulse generator as defined in claim 24 wherein said flyback transformer includes a primary having first and second terminals and a secondary, said primary first terminal being coupled to said depletable power source and said secondary being coupled to said storage capacitor means, and wherein said charging circuit further includes switching means for periodically coupling said primary second terminal to common potential in response to said low duty cycle control voltage.

26. A pulse generator as defined in claim 25 wherein said charging circuit further includes rectifying means coupling said secondary to said storage capacitor means.

27. A pulse generator as defined in claim 26 wherein said rectifying means comprises a diode.

28. A pulse generator as defined in claim 25 wherein said low duty cycle control voltage includes a stream of low duty cycle clock pulses.

29. A pulse generator as defined in claim 28 wherein said charging circuit further includes first means including a coupling transformer for conveying the leading edges of said clock pulses to said switching means for closing said switching means and a second means for conveying the trailing edges of said clock pulses to said switching means for opening said switching means.

30. A pulse generator as defined in claim 29 wherein said switching means comprises a field-effect transistor having a gate and wherein said first and second means are coupled between said oscillator means and said gate.

31. A pulse generator as defined in claim 30 wherein said oscillator means includes a charge control input for receiving a control input signal and wherein said oscillator is responsive to the receipt of said control input signal for providing said stream of low duty cycle clock pulses.

32. A pulse generator for use in an implantable atrial defibrillator for providing cardioverting electrical energy to the atria of a heart through lead means associated with the atria of the heart, said pulse generator comprising:

a depletable, low voltage, power source;
oscillator means for generating a low duty cycle control voltage;
charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor;
switch means for selectively coupling said storage capacitor means to said lead means for applying a portion of said stored electrical energy to the atria of the heart through said lead means for cardioverting the atria of the heart, and
voltage sensing means coupled to said storage capacitor means for sensing the energy stored in said storage capacitor means, said voltage sensing means including amplifier means and voltage divider means coupling said amplifier means to said storage capacitor means for scaling the voltage at said amplifier means and for protecting said amplifier means against damage by the energy stored in said storage capacitor means.

33. A pulse generator for use in an implantable atrial defibrillator for providing cardioverting electrical energy to the atria of a heart through lead means associated with the atria of the heart, said pulse generator comprising:

a depletable, low voltage, power source;
oscillator means for generating a low duty cycle control voltage;
charging means coupled to said power source, said charging means including storage capacitor means for storing electrical energy and a charging circuit responsive to said low duty cycle control voltage for converting said power source low voltage to pulsating high voltage electrical energy and applying said pulsating high voltage electrical energy to said storage capacitor means for storing electrical energy in said storage capacitor; and
switch means for selectively coupling said storage capacitor means to said lead means for applying a portion of said stored electrical energy to the atria of the heart through said lead means for cardioverting the atria of the heart,
the duty cycle of said low duty cycle control voltage electrical energy being substantially equal to eight percent.

34. An implantable atrial defibrillator for providing cardioverting electrical energy to the atria of a heart, said atrial defibrillator comprising:

lead means associated with the atria of the heart;
a battery for providing battery voltage;
oscillator means for generating a low duty cycle control voltage;
charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowing storing electrical energy in said storage capacitor to a level for cardioverting the atria of the heart, said charging circuit storing said electrical energy in said storage capacitor to said level in a time greater than 15 seconds; and
switch means for applying a portion of said stored electrical energy to said lead means for cardioverting the atria of the heart.

35. An atrial defibrillator as defined in claim 34 wherein said charging circuit further includes enable switch means responsive to an enable control signal for coupling said storage capacitor means to said switch means.

36. An atrial defibrillator as defined in claim 34 wherein said charging circuit further includes test means coupled across said storage capacitor and responsive to a test control signal for discharging all of said stored electrical energy.

37. An atrial defibrillator as defined in claim 34 wherein said switch means are responsive to a first control signal for coupling said storage capacitor means to said lead means with a first polarity and responsive to a second control signal for coupling said storage capacitor means to said lead means with a second polarity opposite said first polarity for applying said portion of said stored energy to the atria of the heart with a biphasic waveform.

38. An atrial defibrillator as defined in claim 37 wherein said storage capacitor means includes a positive terminal and a negative terminal, wherein said lead means includes first and second electrodes, and wherein said switch means comprises a first switch coupled between said positive terminal and said first electrode, a second switch coupled between said negative terminal and said second electrode, a third switch coupled between said negative terminal and said first electrode, and a fourth switch coupled between said positive terminal and said second electrode, said first and second switches closing responsive to said first control signal and said third and fourth switches closing responsive to said second control signal.

39. An implantable atrial defibrillator for providing cardioverting electrical energy to the atria of a heart, said atrial defibrillator comprising:
 lead means associated with the atria of the heart;
 a battery for providing battery voltage;
 oscillator means for generating a low duty cycle control voltage;
 charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowly storing electrical energy in said storage capacitor to a level for cardioverting the atria of the heart, said charging circuit storing said electrical energy in said storage capacitor to said level in a time greater than 15 seconds; and
 switch means for applying a portion of said stored electrical energy to said lead means for cardioverting the atria of the heart,
 said charging circuit further including enable switch means responsive to an enable control signal for coupling said storage capacitor means to said switch means and isolation means for coupling said enable control signal to said enable switch means.

40. An atrial defibrillator as defined in claim 39 wherein said isolation means comprises transformer means.

41. An atrial defibrillator as defined in claim 40 wherein said enable switch means comprises a field-effect transistor having a gate coupled to said transformer means for receiving said enable control signal.

42. An atrial defibrillator as defined in claim 41 wherein said enable control signal has a time varying waveform and wherein said charging circuit further includes rectifying means coupling said transformer means to said field-effect transistor gate for rectifying said enable control signal.

43. An atrial defibrillator as defined in claim 42 wherein said rectifying means comprises a diode.

44. An implantable atrial defibrillator for providing cardioverting electrical energy to the atria of a heart, said atrial defibrillator comprising:
 lead means associated with the atria of the heart;
 a battery for providing battery voltage;
 oscillator means for generating a low duty cycle control voltage;
 charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowly storing electrical energy in said storage capacitor to a level for cardioverting the atria of the heart, said charging circuit storing said electrical energy in said storage capacitor to said level in a time greater than 15 seconds; said charging circuit including test means coupled across said storage capacitor and responsive to a test control signal for discharging all of said stored electrical energy and isolation means for coupling said test control signal to said test means.

45. An atrial defibrillator as defined in claim 44 wherein said isolation means comprises transformer means.

46. An atrial defibrillator as defined in claim 45 wherein said test means includes a field-effect transistor having a gate coupled to said transformer means for receiving said control signal.

47. An atrial defibrillator as defined in claim 46 wherein said test control signal has a time varying waveform and wherein said charging circuit further includes rectifying means coupling said transformer means to said field-effect transistor gate for rectifying said test control signal.

48. An atrial defibrillator as defined in claim 47 wherein said rectifying means comprises a diode.

49. An implantable atrial defibrillator for providing cardioverting electrical energy to the atria of a heart, said atrial defibrillator comprising:
 lead means, including first and second electrodes, associated with the atria of the heart;
 a battery for providing battery voltage;
 oscillator means for generating a low duty cycle control voltage;
 charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowly storing electrical energy in said storage capacitor to a level for cardioverting the atria of the heart, said charging circuit storing said electrical energy in said storage capacitor to said level in a time greater than 15 seconds;
 switch means for applying a portion of said stored electrical energy to said lead means for cardioverting the atria of the heart, said switch means being responsive to a first control signal for coupling said storage capacitor means to said lead means with a first polarity and responsive to a second control signal for coupling said storage capacitor means to said lead means with a second polarity opposite said first polarity for applying said portion of said stored energy to the atria of the heart with a biphasic waveform, said switch means comprising a first switch coupled between said positive terminal and said first electrode, a second switch coupled between said negative terminal and said second electrode, a third switch coupled between said negative terminal and said first electrode, and a fourth switch coupled between said positive terminal and said second electrode, said first and second switches closing responsive to said first control signal and said third and fourth switches closing responsive to said second signal; and isolation means for coupling said first control signal to said first and second switches and for coupling said second control signal to said third and fourth switches.

50. An atrial defibrillator as defined in claim 49 wherein said first, second, third, and fourth switches each comprise a field-effect transistor.

51. A atrial defibrillator as defined in claim 49 wherein said isolation means comprises a first transformer including a primary for receiving said first control signal, a first secondary coupled to said first switch and a second secondary coupled to said second switch and wherein said isolation means further includes a second transformer including a primary for receiving said second control signal, a first secondary coupled to said third switch, and a second secondary coupled to said fourth switch.

52. An atrial defibrillator as defined in claim 51 wherein said first and second control signals have time varying waveforms and wherein said switch means includes first rectifying means coupling said first transformer first secondary to said first switch, second rectifying means coupling said first transformer second secondary to said second switch, third rectifying means coupling said second transformer first secondary to said third switch, and fourth rectifying means coupling said second transformer second secondary to said fourth switch, said first and second rectifying means rectifying said first control signal and said third and fourth rectifying means rectifying said second control signal.

53. An atrial defibrillator as defined in claim 52 wherein each said first, second, third, and fourth rectifying means comprises a diode.

54. An implantable atrial defibrillator for providing cardioverting electrical energy to the atria of a heart, said atrial defibrillator comprising:
lead means associated with the atria of the heart including first and second electrodes;
a battery for providing battery voltage;
oscillator means for generating a low duty cycle control voltage;
charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowing storing electrical energy in said storage capacitor to a level for cardioverting the atria of the heart, said charging circuit storing said electrical energy in said storage capacitor to said level in a time greater than 15 seconds; and switch means for applying a portion of said stored electrical energy to said lead means for cardioverting the atria of the heart, said switch means including a first output and a second output, said second output being coupled to said second electrode and said switch means including a resistor coupled across said first and second outputs and a pair of anti-parallel diodes coupling at least one of said outputs to one of said electrodes.

55. An implantable atrial defibrillator for providing cardioverting electrical energy to the atria of a heart, said atrial defibrillator comprising:
lead means associated with the atria of the heart;
a battery for providing battery voltage;
oscillator means for generating a low duty cycle control voltage;
charging means coupled to said battery, said charging means including storage capacitor means for storing electrical energy and a charging circuit including a flyback transformer responsive to said low duty cycle control voltage for converting said battery voltage to pulsating high voltage electrical energy and applying said high voltage electrical energy to said storage capacitor means for slowly storing electrical energy in said storage capacitor to a level for cardioverting the atria of the heart, said charging circuit storing said electrical energy in said storage capacitor to said level in a time greater than 15 seconds; and switch means for applying a portion of said stored electrical energy to said lead means for cardioverting the atria of the heart.

56. An atrial defibrillator as defined in claim 55 wherein said flyback transformer includes a primary having first and second terminals and a secondary, said primary first terminal being coupled to said battery and said secondary being coupled to said storage capacitor means, and wherein said charging circuit further includes switching means for periodically coupling said primary second terminal to common potential in response to said low duty cycle control voltage.

57. An atrial defibrillator as defined in claim 56 wherein said charging circuit further includes rectifying means coupling said secondary to said storage capacitor means.

58. An atrial defibrillator as defined in claim 57 wherein said rectifying means comprises a diode.

59. An atrial defibrillator as defined in claim 57 wherein said charging circuit further includes first means including a coupling transformer for conveying the leading edges of said clock pulses to said switching means for closing said switching means and a second means for conveying the trailing edges of said clock pulses to said switching means for opening said switching means.

60. An atrial defibrillator as defined in claim 59 wherein said switching means comprises a field-effect transistor having a gate and wherein said first and second means are coupled between said oscillator means and said gate.

61. An atrial defibrillator as defined in claim 60 wherein said oscillator means includes a charge control input for receiving a control input signal and wherein said oscillator is responsive to the receipt of said control input signal for providing said stream of low duty cycle clock pulses.

62. An atrial defibrillator as defined in claim 56 wherein said low duty cycle control voltage includes a stream of low duty cycle clock pulses.

63. An implantable atrial defibrillator for providing cardioverting electrical energy to the atria of a heart, said atrial defibrillator comprising:

lead means associated with the atria of the heart;

a battery for providing battery voltage;

oscillator means for generating a low duty cycle control voltage;

charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowing storing electrical energy in said storage capacitor to a level for cardioverting the atria of the heart, said charging circuit storing said electrical energy in said storage capacitor to said level in a time greater than 15 seconds;

switch means for applying a portion of said stored electrical energy to said lead means for cardioverting the atria of the heart; and voltage sensing means coupled to said storage capacitor means for sensing the energy stored in said storage capacitor means, said voltage sensing means including amplifier means and voltage divider means coupling said amplifier means to said storage capacitor means for scaling the voltage at said amplifier means and for protecting said amplifier means against damage by the energy stored in said storage capacitor means.

64. An atrial defibrillator as defined in claim 34 wherein the duty cycle of said low duty cycle control voltage is less than fifty percent.

65. An atrial defibrillator as defined in claim 64 wherein said duty cycle is equal to or less than thirty percent.

66. An implantable atrial defibrillator for providing cardioverting electrical energy to the atria of a heart, said atrial defibrillator comprising:

lead means associated with the atria of the heart;

a battery for providing battery voltage;

oscillator means for generating a low duty cycle control voltage;

charging means coupled to said battery, said charging means including storage capacitor means for storing electrical energy and a charging circuit responsive to said low duty cycle control voltage for converting said battery voltage to pulsating high voltage electrical energy and applying said high voltage electrical energy to said storage capacitor means for slowly storing electrical energy in said storage capacitor to a level for cardioverting the atria of the heart, said charging circuit storing said electrical energy in said storage capacitor to said level in a time greater than 15 seconds; and switch means for applying a portion of said stored electrical energy to said lead means for cardioverting the atria of the heart, the duty cycle of said low duty cycle pulsating low voltage electrical energy being substantially equal to eight percent.

* * * * *